US007604957B2

(12) United States Patent
Fine

(10) Patent No.: US 7,604,957 B2
(45) Date of Patent: *Oct. 20, 2009

(54) METHOD FOR DIAGNOSING IMMUNOLOGIC FOOD SENSITIVITY

(76) Inventor: Kenneth D. Fine, 6919 Pasadena Ave., Dallas, TX (US) 75214

( * ) Notice: Subject to any disclaimer, the term of this patent is extended or adjusted under 35 U.S.C. 154(b) by 13 days.

This patent is subject to a terminal disclaimer.

(21) Appl. No.: 11/899,670

(22) Filed: Sep. 7, 2007

(65) Prior Publication Data

US 2007/0298447 A1 Dec. 27, 2007

Related U.S. Application Data

(63) Continuation of application No. 10/670,100, filed on Sep. 24, 2003, now abandoned, which is a continuation of application No. 09/798,557, filed on Mar. 2, 2001, now Pat. No. 6,667,160.

(51) Int. Cl.
*G01N 33/533* (2006.01)
(52) U.S. Cl. .................. 435/7.92; 435/7.1; 435/7.9; 435/7.94; 435/7.93; 435/971; 436/513; 436/514; 436/518; 436/811
(58) Field of Classification Search ................ 435/7.92, 435/7.1, 7.9, 7.94, 7.93, 971; 436/513, 514, 436/518, 811
See application file for complete search history.

(56) References Cited

OTHER PUBLICATIONS

Andre et al., Allergy. 1995. 50:328-333.*
Picarelli, Antonio, et al.; Gluten-Sensitive Disease with Mild Enteropathy; Gastroenterology 1996; 111; pp. 608-616.
Cooper, B. T., et al.; Gluten-Sensitive Diarrhea Without Evidence of Celia Disease; Gastroenterology 1980; 79; pp. 801-806.
Maiuri L., et al.; Definition of the Initial Immunologic Modifications Upon in Vitro Gliadin Challenge in the Small Intestine of Celiac Patients; Gastroenterology 1966; 110; pp. 1368-1378.
Ferguson, A., et al.; Clinical and Pathological Spectrum of Coeliac Disease—Active, silent, latent, potential; Gut 1993; 34; pp. 150-151.
Ventura, Alessandro, et al.; Duration of Exposure to Gluten and Risk for Autoimmune Disorders in Patients with Celiac Disease; Gastroenterology Aug. 1999; 117(2); pp. 297-303.
Fine, Kenneth D., et al..; The Genetic and Histopathologic Relationship of Microscopic Colitis and Celiac Sprue or Refractory Sprue; Gastroenterology 1999; 116; A879. (Abstract).
Fine, Kenneth D., et al.; High Prevalence of Celiac Sprue-Like HLA-DQ Genes and Enteropathy in Patients with the Microscopic Colitis Syndrome; Am J Gastroenterol 2000; 95; pp. 1974-1982.
Fine, Kenneth D., et al.; The Prevalence and Causes of Chronic Diarrhea in Patients with Celiac Sprue Treated with a Gluten-Free Diet; Gastroenterology 1997; 112; pp. 1830-1837.
Fine, Kenneth D., et al.; Colonic Histopathology in Untreated Celiac Sprue or Refractory Sprue: Is it Lymphocytic Colitis or Colonic Lymphocytosis?; Human Pathology 1998; 29; pp. 1433-1440.

O'Mahony, S., et al.; Dissociation Between Systemic and Mucosal Humoral Immune Responses in Coeliac Disease; Gut; Jan. 1991; 32(1) pp. 29-235.
Dickey, W., et al.; Reliance on Serum Endomysial Antibody Testing Underestimates the True Prevalence of Coeliac Disease by One Fifth; Scand J. Gastroenterol Feb. 2, 2000; 181-183. Review.
Rostami, Kamran, et al.; Sensitivity of Antiendomysium and Antigliadin Antibodies in Untreated Celiac Disease; Am J Gastroenterol; Apr. 1999; 94(4); pp. 888-894.
Green, PHR, et al; Detection of Antiendomysial Antibodies in Adult Celiacs Depends on Histologic and Clinical Disease Severity; Gastroenteroloy; 116; A883; Abstract, 1999.
Prasad, Shyam, et al.; Adult Endomysial Antibody-Negative Coeliac Disease and Cigarette Smoking; Eur J Gastroenterol Hepatol; Jun. 2001; 13(6); pp. 667-671.
Dieterich, Walburga, et al.; Autoantibodies to Tissue Transglutaminase as Predictors of Celiac Disease; Gastroenterology 1998; 115; pp. 1317-1321.
Sulkanen, Satu, et al.; Tissue Transglutaminase Autoantibody Ensyme-Linked Immunosorbent Assay in Detecting Celiac Disease; Gastroenterology 1998; 115; pp. 1322-1328.
Troncone, Ricardo, et al.; Anti-Gliadin Antibodies; J Pediatric Gastroenterol Nutr 1991; 12; pp. 150-158.
Andre F, et al.; IgE in Stools as Indicator of Food Sensitization; April; 50(4); 328-333, Allergy. 1995.
Sasai, K., et al.; Fecal IgE Levels in Infants at 1 Month of Age as Indicator of Atopic Disease; Allergy; Oct. 1994; 49;(49); pp. 791-794.
Kolmannskog, S., et al.; Immunoglobulin E in Extracts of Feces from Children; Inter. Archives of Allergy and Applied Immunology; 1984; 74(1); pp. 50-54.
Kolmannskog, S., et al.; The Excretion of IgE with Feces from Healthy Individuals and from Others with Allergy and Diseases Affecting the Intestinal Tract; Int. Archives of Allergy and Applied Immunology; 1986; 79(4); pp. 357-364.
Vaden, Shelly, et al.; Food Hypersensitivity Reactions in Soft Coated Wheaten Terriers with Protein-Losing Enteropathy or Protein-Losing Nephropathy or Both: Gastroscopic Food Sensitivity Testing, Dietary Provocation, and Fecal Immunoglobulin E; J Vet Inter. Med. 2000; January-February; 14(1); pp. 60-67.

(Continued)

*Primary Examiner*—Bao-Thuy L Nguyen
(74) *Attorney, Agent, or Firm*—Storm LLP; Paul V. Storm, Esq.; Mark D. Perdue, Esq.

(57) ABSTRACT

A method for food sensitivity panel testing (for sensitivities other than gluten sensitivity) by detecting IgA antibodies in serum is disclosed. A method for testing stool samples for the presence of particular antibodies, which is more sensitive and less invasive than prior art testing methods, is also disclosed for diagnosing immunologic food sensitivities. These methods of diagnosis may be used alone or in combination to further enhance the accuracy of diagnosis.

17 Claims, No Drawings

OTHER PUBLICATIONS

Kolmannskog, S, et al.; Immunoglobulin E in Feces from Children with Allergy. Evidence of Local Production of IgE in the gut; International Archives Allergy Applied Immunology; 1985; 76(2); pp. 133-137.

Haas, L., et al., Increased Concentrations of Fecal Anti-Gliadin IGA Antibodies in Untreated Celiac Disease; Clinical Chemistry; Apr. 1993; 39(4); pp. 696-697.

Picarelli, Antonio et al.; Antiendomysial Antibody Detection in Fecal Supernatants; Gastroenterology 2000; 118; A 370; vol. 118; No. 4.

* cited by examiner

METHOD FOR DIAGNOSING IMMUNOLOGIC FOOD SENSITIVITY

CROSS REFERENCE TO RELATED APPLICATIONS

This application is a continuation of U.S. patent application Ser. No. 10/670,100, filed Sep. 24, 2003, now abandoned which is a continuation of U.S. patent application Ser. No. 09,798,557, filed Mar. 2, 2001, (now U.S. Pat. No. 6,667, 160). Each application is hereby incorporated by reference for all purposes.

TECHNICAL FIELD OF THE INVENTION

The invention relates to diagnosing immunologic food or drug sensitivities and their related intestinal diseases or disorders and noninvasive testing for such. In particular, the invention relates to a method for diagnosing immunologic food sensitivity by testing stool for the presence of antibodies. The invention also relates to identifying immunologic food sensitivities, and their related intestinal diseases or disorders, based on the presence of IgA antibodies in blood, the presence of certain other related disorders or diseases, the presence of certain HLA alleles, or based on failure to respond to bismuth subsalicylate treatment of microscopic colitis or a relapse of microscopic colitis after bismuth subsalicylate treatment.

BACKGROUND OF THE INVENTION

Persons with a variety of immunologic food or drug sensitivities, and related intestinal diseases or disorders, may experience a number of ill effects when a particular food or drug substance, or ingredient in the food or drug, is ingested. The ill effects from an allergy (also called immediate or type I hypersensitivity) to a particular food or drug substance or ingredient usually causes rapid development of symptoms including shortness of breath, hives, swelling of the mouth and throat, and sometimes abdominal pain and diarrhea. This form of food allergy traditionally has been diagnosed by skin testing or by measuring IgE antibodies in the blood directed against the food in question. However, chronic immunologic sensitivity to a food involving T and B lymphocytes as part of the chronic cell mediated immune system (also called delayed or type IV hypersensitivity) may include overt symptoms such as abdominal pain, diarrhea, constipation, and weight loss, and may also include less noticeable effects stemming from malabsorption of fluids and dietary nutrients, such as osteoporosis, anemia, or vitamin deficiencies. Without proper diagnostic testing, which currently is limited to invasive means such as blood or serum testing or endoscopic intestinal biopsy, a person may not realize that he or she has an immunologic food sensitivity or immunologic drug sensitivity and may unknowingly continue to consume the triggering food or drug, which may have long term health implications.

For purposes of this background description, the summary of the invention, and the claims no distinction is drawn between an immunologic food or drug sensitivity and the related intestinal disease or disorder stemming from the immune system's reaction to the food or drug ingredient and they are collectively referred to as an immunologic food sensitivity or immunologic drug sensitivity. The description provided is primarily related to immunologic food sensitivities, but it is recognized that certain drugs or ingredients in drugs also trigger immunologic reactions creating an immunologic drug sensitivity similar to such a food sensitivity.

One such immunologic food sensitivity is gluten sensitivity, or more severely, the intestinal disease celiac sprue. Celiac sprue results from an immunologic reaction to dietary gluten contained in wheat, barley, rye, and oats, that results in any degree of intestinal histopathology. By current definitions and classic descriptions, the gluten-induced immunologic process causes villous atrophy and inflammation of the small intestine, in turn, resulting in diarrhea and weight loss from malabsorption of fluid, electrolytes, and dietary nutrients. Despite the fact that chronic diarrhea is the most common symptom of celiac sprue in its classic, villous atrophic, form, there have been no studies of the prevalence of celiac sprue or other immunologic food sensitivities in patients presenting to physicians with chronic diarrhea or other common gastrointestinal symptoms. Additionally, there are no adequate methods in the prior art to diagnose or noninvasively test for immunologic food sensitivities when the patient presents with little or no common gastrointestinal symptoms or when the symptoms are also attributable to other diseases. This frequently results in either no diagnosis or the missed diagnosis of an immunologic food sensitivity.

In recent years it has been discovered that many if not most individuals with celiac sprue do not have diarrhea or weight loss, but instead have other signs and symptoms such as vague abdominal pain, nausea, chronic fatigue, constipation, growth retardation of children, iron deficiency anemia, osteoporosis, seizures or other neurologic disorders, or elevated liver enzyme levels in serum. Some patients may have no signs or symptoms whatsoever.

Furthermore, patients with gluten sensitivity may not have the fully developed intestinal lesion associated with celiac sprue, instead possessing minimally inflamed or even normal small intestinal histology. Therefore, the immunologic food sensitivity of these patients may not be properly diagnosed using known testing methods, such as endoscopic intestinal biopsy and blood or serum testing. Additionally, these patients may present with other immunologic diseases such as autoimmune diseases of skin, liver, joints, kidneys, pancreas, and/or thyroid among others, microscopic colitis, or hepatitis C-induced liver disease, which according to known methodologies has furthered the misdiagnosis of immunologic food sensitivities in the past. However, the exact prevalence of gluten sensitivity or celiac sprue in patients presenting with these immune disorders is unknown, and the full spectrum of such gluten sensitivity, particularly that with fewer classic features, is not adequately addressed in the prior art.

Traditionally, celiac sprue has been regarded as a severe malabsorptive condition of the small intestine that presents clinically mainly with diarrhea and significant weight loss. Although in the U.S. this concept of the disease is still widely held, in Europe it has become recognized that celiac sprue does not always present in traditional fashion, but instead may manifest with mild gastrointestinal or constitutional symptomatology, or asymptomatically in association with other disorders as mentioned above. For this reason, European physicians, especially those in geographic areas where celiac sprue has been thought to be endemic, such as Ireland, U.K., Italy, and Scandinavia, have had a higher diagnostic index of suspicion of celiac sprue in their patients than American physicians have had, and consequently diagnose more cases than traditionally has been done in American institutions. Moreover, in several screening studies of normal subpopulations of these European countries, the disease prevalence of celiac sprue has averaged about 400 per 100,000 population (1 in 250 persons).

By comparison, from limited retrospective information from a single U.S. quaternary care referral center, celiac sprue was calculated to have a prevalence of 22 per 100,000 (1 in 4000-5000) among the American population. However, a group of 2000 blood donors from the U.S. displayed a serologic pattern suggestive of celiac sprue with a frequency of 1 in 250, similar to the prevalence of the disease in European studies. Although, these blood donors were not evaluated clinically, so that the diagnosis of celiac sprue was not formally confirmed, these results suggest that celiac sprue may be present in a large number of undiagnosed Americans. Moreover, serologic data from 228 individuals from a shopping mall were screened by Applicant for celiac sprue. This screening revealed one individual with both antigliadin and anti-tissue transglutaminase antibodies, which are known indicators of gluten sensitivity or celiac sprue, who was subsequently found by small intestinal biopsy to have a mild lesion of celiac sprue, and 28 others with antigliadin antibodies, without anti-tissue transglutaminase antibodies, which is indicative of gluten sensitivity, but not the more severe celiac sprue. Over 40% of these latter 28 patients had steatorrhea and mild small intestinal inflammation. These data indicate that the prevalence of celiac sprue in the general U.S. population is similar to that in Europe, about 1 in 225-250 persons, with milder forms of clinically important gluten sensitivity even more prevalent.

It has been known that celiac sprue occurs almost exclusively in patients possessing certain HLA class II alleles, namely HLA-DQ2 or -DQ8. The protein products of these genes, located on the surface of antigen presenting cells, are involved in the pathogenesis of the disease by binding gliadin as the initial step in the inflammatory reaction. The prevalence of these HLA genes in the general American population, as confirmed by analysis of more than 400 normal controls, is 42% (30% for DQ2, 12% for DQ8). From these figures, a large portion of the American population is genetically capable of gliadin-sensitivity. Thus, it is likely that celiac disease has a prevalence of 1 in 250 people in the U.S., especially considering that the majority of Caucasians, the race thought to be primarily affected by the disease, living in America are descendants of European immigrants. Most of the Hispanic population of the United States also has a genetic lineage from Western Europe; however, there is no published data regarding the prevalence of celiac sprue in this rapidly increasing subset of the U.S. population. Preliminary data in patients with liver disease suggests that Hispanics, at least those encountered in Texas which are mostly Mexican-Americans, may have the highest prevalence of celiac sprue of any racial subset in America. Furthermore, as will be discussed in detail below, Applicant has identified other HLA alleles and allelic combinations predisposing to gluten sensitivity or other chronic immunologic/autoimmune diseases. The prevalence of these genotypes in the U.S. general population approaches 75%.

Thus, because of the sometimes protean manifestations of celiac sprue, a generally low index of disease suspicion among the American medical community, and the commonality of the celiac-predisposing HLA genes, it is likely that gliadin sensitivity actually is relatively common, and that mildly symptomatic celiac sprue is under diagnosed by practicing physicians. Thus, there is a need to establish alternate and improved methods of diagnosing such immunologic food sensitivities so that proper treatment may be obtained.

In addition to the need to identify the correct target populations to be screened for gluten an other food sensitivities, the most accurate method by which this screening should be carried out, and how and when positive screening tests should be followed up, also require determination. The current standard by which patients are identified as having gluten sensitivity and the method most commonly employed to screen asymptomatic individuals is analysis of serum for the presence of IgG or IgA antibodies to gliadin and IgA antibodies to tissue transglutaminase, the latter by either immunofluorescence when it is called antiendomysial antibody or more recently by the more objective ELISA (enzyme-linked immunosorbent assay) method. The current standard for diagnosing other food sensitivities is by analysis of serum for the presence of IgE or IgG antibodies to the suspect foods, or assessing for IgE antibodies via skin prick testing. These methods are well known in the art.

While these antibody tests, particularly antitissue transglutaminase antibodies, are highly sensitive and specific in populations known to have the villous atrophic form of celiac sprue, these known methods of diagnosis and testing, including testing coupled with endoscopic intestinal biopsy, are inadequate to diagnose patients with milder forms of gluten sensitivity and less small intestinal damage, but who still have troubling symptoms and/or important pathophysiologic consequences. These known tests and diagnosis methods are particularly inadequate considering many patients with mild gluten sensitivity do not have all or any of these antibodies in serum, compared to patients with more developed intestinal damage. This is particularly problematic as the majority of gluten sensitive individuals are likely affected in these milder ways.

Complete knowledge is also lacking regarding the proper approach to the converse situation, i.e., patients with antigliadin and/or antitissue transglutaminase antibodies in serum with minimal or no detectable intestinal histopathology, most of whom have mild or no symptoms. Furthermore, the true significance of having serum antigliadin antibodies without antitissue-transglutaminase antibodies also has been unknown. For these reasons, there has been a need to develop more sensitive and specific methods of identifying and properly diagnosing those individuals in screened populations who have pathophysiologic consequences of immunologic gluten sensitivity but perhaps who do not yet have fully developed celiac sprue, and hence, would have negative screening tests by current methods and criteria.

SUMMARY OF THE INVENTION

The invention provides a method of diagnosing immunologic food sensitivities and related diseases or disorders based on the presence of certain other related disorders or immunologic diseases, based on the presence of certain HLA alleles, or based on a failure to respond to bismuth subsalicylate treatment for microscopic colitis or a relapse after such treatment. The invention also provides a diagnostic fecal testing method for immunologic food or drug sensitivities, as well as using serum IgA antibodies (many of which are of intestinal origin) for food sensitivity panel testing. Serum testing for IgA antibodies according to the invention, rather than IgE or IgG antibodies under the current state of the art, applies to testing for a wide range of food sensitivities (other than gluten sensitivity, as testing for IgA antibodies to gliadin and IgA antibodies to tissue transglutaminase are known in the art). Serum testing methods for the detection of antibodies are well known in the art.

Although the discussion of the invention primarily relates to gluten sensitivity or celiac sprue, it is recognized that these methodologies may be applied to identify and test for other immunologic food sensitivities. Once such food sensitivity is sensitivity to dietary yeast, particularly Saccharomyces cervesiae (the yeast utilized in baker's and brewer's yeast, as well as to make fermented foods such as sauerkraut and others). Other such food sensitivities include sensitivities to milk and eggs, specifically sensitivities to lactalbumin, casein, bovine serum albumin, and ovalbumin. Additionally, it is recognized that the method of the invention may be applied to identify immunologic drug sensitivities as certain ingredients in drugs trigger immunologic reactions just as certain food substances.

Diagnosing Immunologic Food Sensitivities and Related Diseases Based on the Presence of Other Disease or Disorder In one aspect of the invention, patients at risk for immunologic food sensitivities are identified and the immunologic food sensitivities are diagnosed based on the presence of certain other immunologic or hepatic diseases or disorders. It is important to identify certain target groups of the population or patients that are at higher risk of having immunologic food sensitivities so that these groups may be tested and properly diagnosed and treated. Known methods for identifying and diagnosing immunologic food sensitivities, such as serum or blood testing and endoscopic intestinal biopsy, and their inadequacies have been previously discussed. Another known method of identifying immunologic food sensitivities is based on the presence of symptoms; however as the symptoms of many of gastrointestinal related diseases overlap, an accurate diagnosis based on symptoms may be difficult.

Frequently, patients with immunologic food sensitivities also have other related diseases or disorders. In such cases, treatment of the related disease or disorder may not be entirely effective to alleviate symptoms. There may be residual symptoms stemming from the undiagnosed and untreated food sensitivity, rather than the treated disease or disorder. Therefore, according to the invention, an immunologic food sensitivity may be diagnosed, and therefore properly treated, based on the presence of certain other diseases or disorders. Additionally, according to the invention, a patient at risk for an immunologic food sensitivity may be identified by the diagnosis of certain other diseases or disorders, particularly those diseases or disorders that presents symptoms, such as malabsorption of fluids or dietary nutrients, vitamin deficiency, osteoporosis, fatigue, anemia, diarrhea, weight loss, bloating, flatulence, abdominal pain, constipation, nausea, growth retardation in children, seizures, or other unexplained neurologic symptoms, that are similar to the symptoms of immunologic food sensitivities. The methods for testing or diagnosing the immunologic or hepatic diseases or disorders described herein are well known in the art and these methods are not discussed by Applicant.

As previously discussed, one such food sensitivity that is commonly undiagnosed or misdiagnosed is gluten sensitivity, or the related disease celiac sprue, which is a more severe form of gluten sensitivity with associated small intestinal damage. There is strong evidence that certain target groups may have a risk for gluten sensitivity or celiac sprue many times higher than asymptomatic individuals in the general population. The reason for this relates to the fact that there are many, mostly immunologic, diseases that are similarly linked to the celiac-related HLA-DQ2 and DQ8 alleles, and to the alleles identified by Applicant to predispose to gluten sensitivity; these include HLA-DQ 1,3 (including the subtypes -DQ1,7, -DQ1,8, and -DQ 1,9), HLA-DQ 1,1, and at least two subtypes of the HLA-DQ 1 allele identified by molecular analysis as HLA-DQB1*0501 and HLA-DQB1*0602. Two examples of diseases previously identified to share this genetic relationship and known to pose an elevated relative risk of celiac sprue are diabetes mellitus type I and Sjogren's syndrome. Furthermore, it has been shown that the longer persons with celiac sprue go undiagnosed and continue to eat gluten, the more prevalent were other associated autoimmune diseases such as diabetes, arthritis, and psoriasis, among many others.

Applicant has identified microscopic colitis to be another disease associated with these HLA-DQ alleles, and this immunologic colonic disease poses a heightened concomitant risk of gluten sensitivity. Furthermore, patients presenting to medical practitioners with any one of the number of potential signs or symptoms of active celiac sprue also should have a higher prevalence of the disease than asymptomatic people. Foremost on this symptom list is chronic diarrhea; however, there have been no studies of the prevalence of celiac sprue in patients with chronic diarrhea. Another target population identified by Applicant is patients carrying a diagnosis of irritable bowel syndrome or having symptoms of irritable bowel syndrome since the symptoms of mild celiac sprue, such as abdominal gaseous pain, occasional diarrhea, and sometimes constipation, cannot be distinguished from those of irritable bowel syndrome. Preliminary data indicates that a high percentage of patients diagnosed with irritable bowel syndrome have antigliadin antibodies in serum which is indicative of gluten sensitivity and celiac sprue. Somewhat unexpectedly, another patient subset identified by Applicant to have a high prevalence of gluten sensitivity by serology is patients diagnosed with gastroesophageal reflux or having gastroesophageal reflux symptoms. Crohn's disease patients and those with alcoholism were also identified by Applicant to have a greater frequency of gluten sensitivity than normal and other patient control participants.

In a previous study carried out by the Applicant, 78 patients with treated celiac sprue were surveyed with respect to their symptoms at the time of their diagnosis. Eighty-three percent stated they had diarrhea prior to being diagnosed with celiac sprue. In the same study, 121 randomly selected people from a Texas city's population were surveyed regarding their stool habits. One percent said they passed liquid stools daily, and another 4% stated they passed loose or watery stools at least three times a week for greater than a continuous six-month period. Thus, chronic diarrhea probably is not rare but may be present in about 5% of Americans or nearly 14 million people. If even a small fraction of this chronic diarrhea is the result of dietary gluten ingestion, then a major impact can be made on the gastrointestinal health of Americans if screening tests could easily and accurately determine who may benefit from dietary gluten withdrawal or withdrawal of another triggering substance, and practitioners applied them on a wide scale basis.

Microscopic colitis (including lymphocytic colitis and collagenous colitis) is a chronic diarrheal syndrome associated with a normal gross/endoscopic appearance of the colon but with inflammation seen on histologic analysis of colonic biopsies. This form of colitis is an important cause of chronic diarrhea, accounting for 10-12% of diagnoses among patients presenting with this symptom to university hospitals in the U.S. Although the clinicopathologic features of microscopic colitis have been well characterized, there has previously been no real knowledge about its pathogenesis. One feature of the colonic inflammatory reaction, intraepithelial lymphocytosis, suggests that the offending agent, whatever it may be, is presented to the mucosa-associated lymphoid tissue of the colon from the luminal side. A parallel can be drawn from the small intestinal pathologic lesion of celiac sprue whereby antigenic protein subfractions of ingested gluten, the prototype of which is gliadin from wheat, stimulate a similar inflammatory reaction in the small intestinal mucosa. Applicant has determined that the inflammatory characteristics of microscopic colitis (mononuclear inflammatory cell infiltration of the lamina propria and intraepithelial lymphocytosis) are strikingly similar to those in the small bowel of celiac sprue. This indicates that a common pathogenesis exists for these syndromes. Therefore, according to the present invention, microscopic colitis, chronic diarrhea, irritable bowel syndrome, and gastroesophageal reflux are indicators that may be used to identify and diagnose gluten sensitivity and other immunologic food sensitivities. Another indicator is chronic liver disease, particularly hepatitis C viral mechanisms, discussed below.

In addition to the histopathologic similarities of the small intestine in celiac sprue and the colon in microscopic colitis, Applicant has discovered striking similarities in the HLA-DQ subtype of patients with these two syndromes. Like the majority of patients with celiac sprue, 62% of patients in a study set with microscopic colitis had HLA-DQ2 (and an additional 30% had another HLA-DQ allelic combination, namely DQ1, 3). The remaining patients had HLA-DQ1,1. The HLA genetic overlap of these two syndromes is one explanation of the coexistence of celiac sprue and microscopic colitis noted to occur in some patients. Thus, some patients with celiac sprue have been found to have microscopic colitis before they eliminated gluten from their diet and others have developed colitis following long periods of gluten abstinence.

Although gliadin may not be the primary etiologic factor for most patients with microscopic colitis (even if they possess a celiac-like HLA type), Applicant has identified, as discussed below, that immunologic gluten sensitivity may cause refractoriness of the colitis to treatment and/or persistent diarrhea that continues until gluten is removed from the diet. Thus, determining which patients with microscopic colitis need to be treated with a gluten-free diet and on what clinical information this should be based, is of practical clinical importance. The use of a diagnosis of microscopic colitis, chronic diarrhea, irritable bowel syndrome, gastroesophageal reflux, alcoholism, Crohn's disease, autism, neuropsychiatric syndromes, or other chronic immunologic/autoimmune diseases as indicators to diagnose gluten sensitivity or other immunologic food sensitivities, may be coupled with the stool testing methods described below as another aspect of the invention, to further enhance the accuracy of immunologic food sensitivity diagnosis. Additionally, the diagnosis of an idiopathic neurologic syndrome, such as seizures, cerebellar degeneration, multiple sclerosis, peripheral neuropathy, and others, is another indicator of gluten sensitivity or other immunologic food sensitivities that may be coupled with the stool testing methods described below to further enhance the accuracy of immunologic food sensitivity diagnosis.

Another clinical setting in which patients have been identified to have an elevated relative risk of celiac sprue is that of elevated hepatic transaminase levels in blood. Although it has been observed for many years that as many as 40% of patients with celiac sprue have elevated liver enzymes at the time of diagnosis, it has been noted only recently that almost 10% of patients presenting to physicians with elevated serum liver transaminase levels of unknown etiology have celiac sprue, and many more may have gluten sensitivity of milder degrees. Indeed, celiac sprue, which has been epidemiologically linked to certain autoimmune liver diseases, has recently been identified to be associated with production of the specific autoantibody antitissue transglutaminase.

While it is possible that immunologic gluten sensitivity and inflammatory damage of the small intestine as a primary event may secondarily cause liver inflammation, evidenced by normalization of elevated serum transaminase levels and resolution of nonspecific hepatic histopathologic inflammation after removal of gluten from the diet in celiac sprue patients so-affected, it is also possible that certain hepatic inflammatory diseases trigger immunologic gluten intolerance and autoimmune attack on the intestine in genetically predisposed individuals. One common hepatic disease, viral hepatitis C, in particular has been identified to lead to secondary autoimmune processes in other parts of the body; infection with the hepatitis C virus has been associated with development of antinuclear antibodies, mixed cryoglobulinemia, and lichen planus of the skin. Additionally, the cell-mediated inflammatory response of a patient with hepatitis C has been linked to T cells restricted to HLA-DQ2, an allele commonly associated with gluten sensitivity. Through testing, Applicant has shown that 1.2% of patients with hepatitis C have celiac sprue compared to 0% in liver control patients. Therefore, hepatitis C is a trigger for the autoimmune reactions that are pathogenic to celiac sprue.

Therefore, according to the present invention, hepatitis C and other hepatic diseases are indicators which may be used to identify and diagnose gluten sensitivity and other immunologic food sensitivities. Further, the use of a diagnosis of hepatitis C or other hepatic disease, as an indicator for gluten sensitivity or other immunologic food sensitivities, may be coupled with the stool testing methods described below as another aspect of the invention, to further enhance the accuracy of immunologic food sensitivity diagnosis.

Diagnosing Immunologic Food Sensitivities and Related Diseases Based on Relapse after Treatment of Microscopic Colitis with Bismuth Subsalicylate Additionally, the use of bismuth subsalicylate (commonly available under the trademark Pepto-Bismol, from Procter and Gamble) has been successfully shown by Applicant to treat microscopic colitis. Microscopic colitis is diagnosed using methods well known in the art or using the method of the invention described herein. According to the treatment regimen developed by Applicant, the patient's microscopic colitis is treated with 3 chewable tablets or swallowed caplets of bismuth subsalicylate taken 3 times a day for about 8 weeks. Three tablespoons three times a day of the liquid form of bismuth subsalicylate would be an equivalent dose. This amount and frequency for bismuth subsalicylate treatment is generally preferred, however other amounts may be used depending on the particular patient being treated. Although an 8-week treatment period is preferred it is recognized that shorter or longer treatment periods may be used.

Trials using bismuth subsalicylate have included patients with long standing celiac sprue complicated by microscopic colitis, and patients who were diagnosed with sprue at the time their colitis was found. Patients known to have celiac sprue, although responding to bismuth subsalicylate treatment for their colitis, displayed a greater tendency to relapse weeks to months after the 8-week treatment period. Although a few of the microscopic colitis patients not known to have celiac sprue have exhibited this same response-relapse pattern to bismuth subsalicylate treatment, this response or failure to respond to the 8-week treatment all together, coupled with the HLA genetic overlap between microscopic colitis and celiac sprue and the presence of abnormal small bowel histology is indicative of immunologic gluten sensitivity. Each of these patients' serum was analyzed for the presence of antigliadin and antitissue transglutaminase antibodies. Only three of these patients had positive serum antibody tests. Therefore, relapsing or refractory colitis patients' stool was tested for the presence of antigliadin and antitissue transglutaminase antibodies. The method for testing the stool according to the present invention is discussed in detail below.

TABLE 1

Diagnostic Parameters in 52 Patients with Microscopic Colitis Stratified by Responsiveness to Treatment with Bismuth Subsalicylate

| Response Pattern | n | HLA-DQ2 or −1,3 | Abnormal Small Bowel | Serum AGA IgA | Fecal AGA IgA | Serum ATTA | Fecal ATTA |
|---|---|---|---|---|---|---|---|
| Response, no relapse | 20 | 15 (75%) | 4 (20%) | 2 (15%) | 15 (75%) | 0 | 12 (60%) |
| Response, relapse | 25 | 25 (100%) | 23 (92%) | 5 (12%) | 21 (84%) | 1 (4%) | 18 (72%) |
| No response | 7 | 7 (100%) | 7 (100%) | 1 (14%) | 7 (100%) | 0 | 7 (100%) |

AGA—antigliadin antibody
ATTA—antitissue transglutaminase antibody

Table 1 compares diagnostic parameters in the relapse patients compared to those who responded to bismuth subsalicylate therapy without relapse. There was a greater percentage of patients with abnormal small bowel histology and fecal antigliadin and antitissue transglutaminase IgA antibody in the relapsing/refractory groups. Based on all of these data, the 32 patients who have displayed some element of refractoriness of their colitis to treatment have been advised to try a gluten-free diet, including the 28 with antigliadin/antitissue transglutaminase antibody in stool. They agreed to try the diet for at least 6 months; 24 experienced a subjective improvement in their diarrhea, abdominal bloating, energy level, and general well-being and have stayed on the diet.

Thus, many patients with microscopic colitis may have mild celiac sprue requiring treatment with a gluten-free diet for complete symptom relief. Therefore, another aspect of the invention uses failure to respond to or a relapse after treatment for microscopic colitis with bismuth subsalicylate as an indicator to diagnose some degree of celiac sprue or immunologic food sensitivity. The use of a failure to respond or a relapse in the microscopic colitis, as an indicator for diagnosis of gluten sensitivity or other immunologic food sensitivities, may be coupled with the stool testing methods described below, to further enhance the accuracy of or confirm diagnosis of an immunologic food sensitivity.

Diagnosing Immunologic Food Sensitivities and Related Intestinal Diseases Based on HLA Gene Testing Results As previously discussed, it is known that celiac sprue, and other immunologic food sensitivities and related intestinal diseases or disorders, occur almost exclusively in patients possessing certain HLA class II alleles, namely HLA-DQ2 or -DQ8. Methods of testing for HLA alleles are well known in the art and are not described herein. The protein products of these genes, located on the surface of antigen presenting cells, are involved in the pathogenesis of the disease by binding gliadin as the initial step in the inflammatory reaction. The prevalence of these HLA genes in the general American population, as confirmed by analysis of more than 400 normal controls, is 42% (30% for DQ2, 12% for DQ8).

In addition to the HLA-DQ2 or -DQ8 alleles, Applicant has discovered that other HLA alleles are prevalent in diseases such as microscopic colitis, and are related to celiac sprue. In particular, HLA-DQ 1,3 (including the subtypes HLA-DQ1, 7, -DQ1,8, and -DQ1,9), HLA-DQ1,1, and at least two subtypes of the HLA-DQ1 allele identified by molecular analysis as HLA-DQB1*0501 and HLA-DQB1*0602HLA-DQ1,3, are indicators of immunologic food sensitivity, particularly gluten sensitivity. The detection of these alleles, through methods well known in the prior art, is used according to the present invention as a further method of diagnosing immunologic food sensitivities and their related diseases, particularly gluten sensitivity, celiac sprue, and microscopic colitis.

Additionally, in Applicant's study of bismuth subsalicylate treatment and relapse of microscopic colitis, Applicant discovered that of the seven patients with refractory microscopic colitis, all of whom had fecal antigliadin or antitissue transglutaminase antibody detected, three patients had an HLA-DQ 1,7 type (one subtype of HLA-DQ 1,3) rather than DQ2. This indicates that the second most common HLA-DQ type in microscopic colitis, DQ1,7, is also an indicator of immunologic reactivity to gluten and other food sensitivities. Based on other data, the same is believed to be true for DQ1,8 and DQ1,9, all of which are subtypes of DQ1,3.

Therefore, it is another aspect of the invention to use prior art methods to detect the presence of HLA-DQ 1,3 (including the subtypes HLA-DQ1,7, -DQ1,8, and -DQ1,9), HLA-DQ1, 1, and at least two subtypes of the HLA-DQ 1 allele identified by molecular analysis as HLA-DQB1*0501 and HLA-DQB1*0602 wherein the detection of any of these alleles is utilized as an indicator in the diagnosis of immunologic food sensitivity and related disease, particularly gluten sensitivity, celiac sprue, or microscopic colitis. The use of these alleles, as diagnostic indicators for gluten sensitivity or other immunologic food sensitivities, may be coupled with the stool testing methods described below, to further enhance the accuracy of immunologic food sensitivity diagnosis.

Diagnosing Immunologic Food or Drug Sensitivity by Testing Fecal Samples for Antibodies The following discussion relates to testing for gluten sensitivity or celiac sprue, as gluten sensitivity and celiac sprue are perhaps the most commonly under diagnosed or misdiagnosed food sensitivities. It is recognized that the method described is equally applicable to other food or drug sensitivities, with the exception that the antibody being screened for varies depending on the particular food or drug sensitivity under diagnosis.

Clinicians and clinical researchers who frequently are asked to evaluate patients with suspected gluten intolerance are quite familiar with individuals who give compelling histories regarding gastrointestinal symptoms provoked by gluten-containing foods, which abate upon withdrawal from gluten, but who have no detectable evidence of celiac sprue by serology or intestinal histology. This scenario has been called gluten-sensitive diarrhea, or more simply, gluten sensitivity. Although such individuals indeed have a mild form of gluten intolerance, which may be due simply to the poor digestability of wheat, there are similar individuals who actually have an element of immunologic reactivity to gluten, i.e., serum and now fecal antigliadin antibodies, but who do not manifest all the features diagnostic of celiac sprue, namely antiendomysial or antitissue transglutaminase antibodies, or a fully developed small intestinal lesion.

Traditionally, screened individuals or patients with isolated antigliadin antibodies in serum were either not biopsied to prove or disprove that they had celiac sprue, or had an intestinal biopsy that was normal or only minimally inflamed and hence were not diagnosed with or treated for celiac sprue. These known approaches result in no diagnosis or a misdiagnosis of immunologic food sensitivities. Therefore, the present invention provides a more sensitive method of testing intestinal physiologic function to be certain that the antigliadin humoral response is not associated with occult intestinal damage, symptoms, and/or pathophysiological consequences, some of which may be irreversible, such as short stature and osteopenia.

A stool sample with isolated antigliadin antibodies indicates that the patient suffers from some degree of immunologic gluten sensitivity or mild celiac sprue, regardless of the results of the serum test. Such patients should avoid ingestion of dietary gluten or other triggering food substance depending on the particular immunologic food sensitivity antibody being tested.

Approximately 10% of randomly selected individuals from the "normal" population have antigliadin antibodies detected in serum. For no logical reason except that such individuals were considered "normal," this has been interpreted to mean that antigliadin antibodies per se have no real clinical significance. However, an alternative interpretation of this scenario is that the 90% without antigliadin antibodies in serum are truly normal with respect to immunologic gliadin reactivity, and that the 10% that possess serum antigliadin antibodies are abnormal relative to the majority. Furthermore, there have been no extensive physiologic and histopathologic studies of patients with isolated antigliadin antibody in serum.

An evaluation of stool by Applicant in such individuals reveals steatorrhea in 43%, and an abnormal small intestinal permeability based on a sucrose absorption test in 56%, even though upper small intestinal histology is normal or only minimally inflamed. This indicates that antigliadin antibody production is abnormal and the gluten sensitivity in such individuals may be associated with intestinal symptoms and/or damage. The same can be said about isolated antigliadin antibodies found in stool, according to the testing methodology discussed below. Thus another aspect of the invention is that isolated presence of antigliadin antibodies (IgG or IgA) detected in serum or stool indicates that clinically important gluten sensitivity is present.

Although about two-thirds of patients with microscopic colitis have a celiac-predisposing HLA class II allele and some degree of small intestinal histopathology, only 13% and 5%, respectively, have detectable antigliadin IgA and antitissue transglutaminase IgA antibody in serum and with low titers. As these IgA antibodies are produced in the intestinal mucosa and secreted into the lumen, a greater percentage of patients may have these antibodies detectable in intestinal effluent, i.e., stool. Using a modified version of an FDA approved ELISA kit, which is well known in the art and commercially available from INOVA Diagnostics, San Diego, Calif., patients with celiac sprue, refractory sprue and microscopic colitis, the microscopic colitis syndrome, and normal volunteers were tested for the presence of antigliadin and antitissue transglutaminase IgA antibody in the stool. The modification of the kit's published method first utilizes stool rather than serum, and utilizes methods of concentrating the stool for enhanced detection of these antibodies. The stool sample is collected after excretion by the patient in an appropriate specimen container.

Applicant's sample collection kit, including instructions and a specimen container, may be order by the patient through Applicant's laboratory, Enterolab. Preferably, the kit is ordered on-line via Applicant's web site on the Internet. Once shipped to the patient, the patient collects a stool sample in the specimen container according to the instructions provided, which may include instruction regarding changes to the patient's diet for a period of time prior to sample collection. The sample is then returned to the lab for testing via the air shipping label and packaging provided. Although this is the preferred method for collecting a sample from a patient, it is recognized that other methods of obtaining a sample may be used within the scope of the invention. Such methods include having the patient physically go to a clinic, lab, doctor's office, or other appropriate medical establishment to provide a stool sample. Additionally, if the clinic, lab, or doctor's office is local relative to the patients' residence, the patient may pick-up instructions and a specimen container for collection of the sample at home and then return the sample for testing.

Once collected and received by the lab, the fecal matter of the sample is then concentrated and screened using the ELISA kit to detect the appropriate antibody based on the particular food sensitivity under diagnosis. With the exception of modifying the handling of the sample prior to testing as described below, the standard method of the ELISA kit is utilized to screen the sample to detect antibodies. The detection of a particular antibody then forms the basis for a diagnosis of the food sensitivity associated with that antibody, for instance the detection of antigliadin IgA or antitissue transglutaminase IgA results in a diagnosis of gluten sensitivity or celiac sprue.

One method of concentrating the stool specimen is to spin the stool in a centrifuge to obtain a watery supernatant. The rotation of the centrifuge is preferably between 13,500 rpm and 20,000 rpm, but other rotation speeds may be used depending on the viscosity of the specimen. The modification of the test kit method involves using the supernatant as an undiluted test specimen, rather than diluting the specimen with the diluent provided in the test kit. Although it is preferred that the specimen be analyzed undiluted, reconstituted lyophilized samples may also be used. The undiluted specimen is added to the test well in an amount approximately equal to the required volume of diluted serum. The sample is then tested for the appropriate antibody, depending on the immunologic food sensitivity being considered for diagnosis.

Another method of concentrating the stool specimen, which is particularly used when the specimen is watery or diarrheal, is to freeze-dry or lyophilize the specimen to solid material and reconstituting it with water at a dry matter to water ratio approximately equal to that of non-diarrheal stool. This dry matter to water ratio is preferably approximately 25% dry matter to 75% water, although other ratios may be used. The sample is then placed in the test well and tested for the appropriate antibody. Compared to proper normal controls, this concentration method enhances the detection of gluten sensitivity in a suspect target diarrheal population, such as microscopic colitis, by approximately 50%, increasing diagnosis through positive testing from 50% to 75%.

The upper limit of "normal" for fecal antigliadin IgA was derived from the mean +2SD of values measured in stools obtained from 13 normal volunteers; the upper limit of "normal" for fecal antitissue transglutaminase was calculated in the same manner. The upper limit for "normal" antigliadin IgA is about 10 units and the upper limit for "normal" antitissue transglutaminase IgA is about 10 units.

Table 2 shows the results of this testing. In the 12 normal volunteers, 25% of the individuals' stools were positive for antigliadin IgA antibody, which indicates that these individuals have undiagnosed gluten sensitivity. "Normal" volunteers with symptoms had an even higher detection rate. Untreated celiac sprue patients had a high percentage, approximately 76%, of antigliadin IgA antibody in serum; while 100% had these antibodies detected in stool. In contrast, patients with refractory sprue or microscopic colitis, had a much higher detection rate of these antibodies in stool compared to the almost non-existent presence in serum. Supportive of the test's accuracy is that treated celiac sprue patients who do not eat gluten and have no symptoms, had the lowest positivity rate. Fecal antigliadin IgG antibody was undetectable in all patients (data not shown in table), supporting the fact that the fecal IgA antibodies are secreted into the intestine rather than nonspecifically leaking from the serum (because if it was a leak of serum antibody into the intestine, IgG antigliadin antibody also would have been detected in stool). Therefore, in one aspect of the invention stool samples are tested for antibodies to detect and diagnose immunologic food sensitivities.

TABLE 2

Antigliadin IgA Antibody Detection Rates in Serum vs. Stool

| Group Tested | n | Serum AGA IgA | Fecal AGA IgA | AGA in stool, not serum |
|---|---|---|---|---|
| Untreated celiac | 17 | 13 (76%) | 17 (100%) | 4 (24%) |
| Refractory | 4 | 1 (25%) | 4 (100%) | 3 (75%) |
| Microscopic Colitis | 46 | 5 (11%) | 35 (76%) | 30 (65%) |
| Normal Volunteers | 12 | 0 (0%) | 3 (25%) | 3 (25%) |
| Symptomatic Non-patients | 8 | 0 (0%) | 6 (75%) | 6 (75%) |
| Treated Celiac Sprue | 11 | 2 (18%) | 1 (9%) | 1 (9%) |
| MC/Treated Sprue | 6 | 0 (0%) | 4 (67%) | 4 (67%) |

AGA—antigliadin antibody

Further, all patients with microscopic colitis and fecal antigliadin and antitissue transglutaminase antibodies had some degree of small intestinal histopathology. In fact, one of these patients, and the one with the most abnormal celiac-like small intestinal biopsies observed in a patient with microscopic colitis, was a middle-aged woman with HLA-DQ2 and fecal antigliadin antibody but no antigliadin or antiendomysial/antitissue transglutaminase antibodies in her serum. This particular patient had gross evidence of villous atrophy, i.e., scalloping of duodenal folds, visualized at the time of her endoscopy.

Recently fecal samples from patients with chronic diarrhea were tested for celiac sprue. Additionally, antigliadin and antitissue transglutaminase antibody tests, which are well known in the art, were used to screen serum in 50 patients with chronic diarrhea and stool in an additional 46. Table 3 shows the results of this analysis. While there was a relative paucity of antigliadin and antitissue transglutaminase antibody test positivity from analysis of serum, a relatively large percentage of patients also had these antibodies detected in stool. Thus, like patients with microscopic colitis, analysis of stool may be more sensitive than tests of serum for detection of antigliadin and antitissue transglutaminase IgA antibodies.

Another antibody detected in stools of patients is an antibody to the yeast present in common baked goods and beer. The yeast is called *Saccharomyces cervesiae*. This, as well as sensitivities to other food substances such as cow's milk (whereby antibodies to lactalbumin, casein, and bovine serum albumin are detected) and chicken's eggs (antibodies to ovalbumin), is another immunologic food sensitivity diagnosable by the method of the invention.

TABLE 3

Frequency of Celiac Sprue Serologic Test Positivity in Patients with Chronic Diarrhea

| | AGA IgG | AGA IgA | AGA IgG or IgA | ATTA IgA |
|---|---|---|---|---|
| Serum Screened (n = 50) | 6 (12%) | 2 (4%) | 8 (16%) | 1 (2%) |
| Stool screened (n = 46) | 0 | 19 (41%) | 19 (41%) | 10 (22%) |

AGA—antigliadin antibody
ATTA—antitissue transglutaminase antibody

The stool sample is preferably tested according to the invention by using the following steps. The stool is homogenized by hand mixing, although it is recognized that other mechanical methods of mixing may be utilized. The stool sample is concentrated, preferably using one of the previously described methods, however, other methods of concentration may be used within the scope of the invention. An aliquot of approximately 20 grams is preferably used as a sample, however it is recognized that other sample sizes may be used. The supernatant will be analyzed for antigliadin and antitissue transglutaminase IgA antibodies, or other appropriate antibodies according to the particular immunologic food or drug sensitivity under diagnosis.

The ELISA serum testing kit, which is also well known in the art, may be utilized to test the stool supernatant. It is preferred that the supernatant be analyzed undiluted through the modification of well-known serum testing methods described. However, reconstituted lyophilized samples may also be used according to the invention. The presence of these antibodies, or other immunologic food sensitivity triggered antibodies depending on which particular food sensitivity is being tested, indicates that the patient does have the particular immunologic food sensitivity. The patient should be treated accordingly by removing the triggering substance from his or her diet or by other methods known in the art.

Although specific parameters and equipment have been discussed in this aspect of the invention, it is understood that the parameters may differ and that different equipment may be used to carry out the disclosed methodologies without deviating from the scope of the invention.

This stool testing method may be combined with one or more of the immunologic food sensitivity diagnosis indicators previously described according to the invention in order to further enhance the sensitivity and accuracy of immunologic food sensitivity diagnosis.

I claim:

1. A method for diagnosing an immunologic food sensitivity comprising the steps of:
    collecting a fecal sample;
    screening the fecal sample to detect the presence of an IgA antibody to a particular food substance; and
    diagnosing the immunologic food sensitivity based on the presence of the antibody, wherein the immunologic food sensitivity is related to an ailment.

2. The method of claim 1 further comprising collecting a testing portion from the fecal sample, wherein the testing portion is the sample in the screening step.

3. The method of claim 2 wherein the testing portion is undiluted.

4. The method of claim 2 further comprising the step of homogenizing the fecal sample prior to the collecting the testing portion step.

5. The method of claim 2 wherein the testing portion is about 20 grams.

6. The method of claim 1 wherein the screening step utilizes an enzyme-linked immunosorbant assay (ELISA) testing kit to detect the presence of the antibody to a particular food substance.

7. The method of claim 2 wherein the screening step utilizes an enzyme-linked immunosorbant assay (ELISA) testing kit to detect the presence of the antibody to a particular food substance.

8. The method of claim 2 wherein the collecting the testing portion step comprises the steps of:
centrifuging the fecal sample;
removing a supernatant portion from the centrifuged fecal sample; and
using the supernatant portion as the testing portion.

9. The method of claim 8 wherein the centrifuging step is performed at a rotation speed dependant upon the viscosity of the sample.

10. The method of claim 8 wherein the rotation speed is between about 13,500 and 20,000 rpm.

11. The method of claim 8 wherein the testing portion is screened undiluted and is about equal to an amount of diluted serum required by standard use of an ELISA kit.

12. The method of claim 2 wherein the collecting the testing portion step comprises the steps of:
freeze-drying the fecal sample to a solid material; and
reconstituting the solid material with water to form a reconstituted testing portion.

13. The method of claim 12 wherein the reconstituted testing portion is about 25% solid material and about 75% water.

14. The method of claim 2 wherein the fecal sample contains more than about 90% water in its excreted state and wherein the collecting the testing portion step comprises the steps of:
freeze-drying the fecal sample to a solid material; and
reconstituting the solid material with water to form a reconstituted testing portion.

15. The method of claim 1 wherein the ailment presents similar symptoms as the immunologic food sensitivity.

16. The method of claim 15 wherein the symptoms are malabsorption of fluids, malabsorption of dietary nutrients, vitamin deficiency, osteoporosis, fatigue, anemia, diarrhea, weight loss, bloating, flatulence, abdominal pain, constipation, nausea, growth retardation in children, seizures, and other unexplained neurologic symptoms.

17. The method of claim 15 wherein the ailment is irritable bowel syndrome, microscopic colitis, chronic diarrhea, chronic liver disease, gastroesophageal reflux, hepatitis C, hepatic disease, Crohn's disease, an autoimmune disease, autism, alcoholism, idiopathic neurologic syndromes, or neuropsychiatric syndromes.

* * * * *